United States Patent
Tong et al.

(12)

(10) Patent No.: US 11,327,070 B2
(45) Date of Patent: May 10, 2022

(54) BLOOD ANALYSIS METHOD, CONTROL DEVICE AND BLOOD CELL ANALYZER (71) Applicants: CHENGDU SHEN MINDRAY MEDICAL ELECTRONICS TECHNOLOGY RESEARCH INSTITUTE CO., LTD, Chengdu (CN); SHENZHEN MINDRAY BIO-MEDICAL ELECTRONICS CO., LTD., Shenzhen (CN)

(72) Inventors: Wenjun Tong, Chengdu (CN); Yijie Yang, Chengdu (CN); Huaming Xu, Chengdu (CN); Xing Shi, Chengdu (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 273 days.

(21) Appl. No.: 16/277,519

(22) Filed: Feb. 15, 2019

(65) Prior Publication Data
US 2019/0178875 A1 Jun. 13, 2019

Related U.S. Application Data (63) Continuation of application No. 14/996,136, filed on Jan. 14, 2016, now Pat. No. 10,215,750, which is a
(Continued)

(30) Foreign Application Priority Data

Jul. 16, 2013 (CN) .......................... 201310298749.4

(51) Int. Cl.
*G01N 33/50* (2006.01)
*G01N 1/18* (2006.01)
(Continued)

(52) U.S. Cl.
CPC ........... *G01N 33/5094* (2013.01); *G01N 1/18* (2013.01); *G01N 1/38* (2013.01); *G01N 15/10* (2013.01);
(Continued)

(58) Field of Classification Search
None
See application file for complete search history.

(56) References Cited

U.S. PATENT DOCUMENTS 4,683,212 A 7/1987 Uffenheimer
5,260,192 A 11/1993 Russell et al.
(Continued)

FOREIGN PATENT DOCUMENTS

CN 1834659 9/2006
CN 101097180 1/2008
(Continued)

OTHER PUBLICATIONS

English machine translation of WO 2004/003517 A1, Le Comte, Roger, Jan. 2004 (Year: 2004).*
(Continued)

*Primary Examiner* — Matthew D Krcha
*Assistant Examiner* — Brittany I Fisher
(74) *Attorney, Agent, or Firm* — Kory D. Christensen (57) ABSTRACT The present disclosure provided a blood cell analyzer, a control device and a blood analysis method thereof. In the method, a first reagent is mixed with a sample to obtain a first testing sample, and then a second reagent is mixed with the first testing sample for a further reaction to get a second testing sample for basophil classification and/or HGB measurement. A blood sample may be tested in one reaction cell through time-division multiplexing technology to obtain four groups leukocytes classification result and HGB result by single detection channel. Thus, the structure of the
(Continued)

analyzer may be greatly simplified on the premise of guaranteeing the performance of the analyzer, the size and cost of the analyzer may reduce and a performance-price ratio of the analyzer may increase.

10 Claims, 5 Drawing Sheets

Related U.S. Application Data continuation of application No. PCT/CN2014/074059, filed on Mar. 25, 2014.

(51) Int. Cl.
| | |
|---|---|
| *G01N 1/38* | (2006.01) |
| *G01N 15/10* | (2006.01) |
| *G01N 15/14* | (2006.01) |
| *G01N 33/72* | (2006.01) |
| *G01N 35/00* | (2006.01) |
| *G01N 15/00* | (2006.01) |
| *G01N 35/10* | (2006.01) |
| *G01N 15/05* | (2006.01) |

(52) U.S. Cl.
CPC ........... *G01N 15/14* (2013.01); *G01N 33/721* (2013.01); *G01N 33/726* (2013.01); *G01N 35/00871* (2013.01); *G01N 35/1097* (2013.01); *G01N 15/1459* (2013.01); *G01N 35/1095* (2013.01); *G01N 2015/008* (2013.01); *G01N 2015/0069* (2013.01); *G01N 2015/055* (2013.01); *G01N 2015/1006* (2013.01); *G01N 2015/1062* (2013.01); *G01N 2015/1486* (2013.01); *G01N 2333/805* (2013.01)

(56) References Cited

U.S. PATENT DOCUMENTS

| | | | |
|---|---|---|---|
| 5,656,499 A * | 8/1997 | Chupp | ................ B01F 5/0453 422/63 |
| 6,232,125 B1 | 5/2001 | Deka et al. | |
| 6,365,106 B1 | 4/2002 | Nagai | |
| 8,916,384 B2 * | 12/2014 | Perez | ................... G01N 35/085 436/180 |
| 2003/0032193 A1 * | 2/2003 | Narisada | ............ G01N 15/1459 436/63 |
| 2006/0210438 A1 | 9/2006 | Nagai | |
| 2008/0180653 A1 * | 7/2008 | Narisada | ............ G01N 15/1459 356/36 |
| 2009/0068726 A1 * | 3/2009 | Magnin | ............... G01N 15/1456 435/288.7 |
| 2010/0129855 A1 | 5/2010 | Kataoka | |
| 2011/0005321 A1 | 3/2011 | Matsumoto | |
| 2013/0171681 A1 | 7/2013 | Shibata | |

FOREIGN PATENT DOCUMENTS

| | | | |
|---|---|---|---|
| CN | 101470108 | | 7/2009 |
| CN | 102300641 | | 12/2011 |
| FR | 2841653 A1 | | 1/2004 |
| WO | WO 91/18086 A1 | | 11/1991 |
| WO | WO-2004003517 A1 * | | 1/2004 ......... G01N 15/1404 |
| WO | WO 2006084472 | | 8/2006 |

OTHER PUBLICATIONS

Restriction Requirement, U.S. Appl. No. 16/277,464, filed Feb. 15, 2019, dated Jan. 14, 2021.

Non-Final Office Action, U.S. Appl. No. 16/277,464, dated Mar. 30, 2021, 26 pages.

* cited by examiner

BLOOD ANALYSIS METHOD, CONTROL DEVICE AND BLOOD CELL ANALYZER

CROSS-REFERENCE TO RELATED APPLICATIONS

This application is a Continuation under 35 U.S.C. § 120 of U.S. patent application Ser. No. 14/996,136, filed Jan. 14, 2016, which is a Continuation of international patent application Ser. No. PCT/CN2014/074059, filed Mar. 25, 2014, which claims priority and benefit of Chinese Patent Application No. 201310298749.4, filed Jul. 16, 2013 in the China Intellectual Property Office, the content of each application is hereby incorporated by reference.

TECHNICAL FIELD

The present disclosure relates to the field of medical technology, more particularly to a blood analyzer, a control device and a blood analysis method.

BRIEF SUMMARY

The present disclosure relates to methods and apparatuses for blood analysis. More particularly, the present disclosure relates to a blood analysis method for a blood analyzer, wherein a first reagent is mixed with a sample to obtain a first testing sample for leukocyte classification, and then a second reagent is mixed with the first testing sample for a further reaction to get a second testing sample for BASO classification and/or HGB measurement. Moreover, the present disclosure relates a control device and a blood analyzer thereof.

BRIEF DESCRIPTION OF THE DRAWINGS

Similar reference characters in drawings refer to the same, functionally similar, and/or structurally similar elements. It should be understood that the drawings are intended to illustrate exemplary embodiments but are not intended to in any way limit the scope of the invention as set forth in the claims.

DETAILED DESCRIPTION

A blood analyzer is used to analyze components in a blood sample, for example counting and classifying leukocytes in the blood sample, measuring hemoglobin (HGB) concentration and so on. Leukocytes in human blood have five groups: lymphocyte, monocyte, neutrophil, basophil and eosinophil, which can be counting and classified into these five groups by the blood analyzer.

Now, there are two methods for classifying leukocytes into five groups. One is single-channel method and the other is two-channel method. In single-channel method, there is only one detection channel for leukocyte classification, and a blood sample reacts with a reagent in one reaction cell to obtain a testing sample, which is transferred to a detection apparatus for obtaining five-group classification information by single detection. In two-channel method, there are one DIFF channel for cell counting & differentiation and one independent BASO channel for basophil detection only. One blood sample is divided into two aliquots, and these two aliquots are reacted with reagents in two reaction cells and detected by two channels respectively, and leukocyte four-group classification result (ie. Leukocytes are classified into four groups, lymphocyte group, monocyte group, neutrophil & basophil group and eosinophil group) is obtained by DIFF channel, and basophil result is obtained by BASO channel and then these two results are combined to obtained five-group classification result.

The single-channel method might have unsatisfied reliability because it might be difficult to differentiate basophils from other cells of leukocytes when other cells are not damaged. In addition, a blood analyzer using the single-channel method might still have independent channel to meet requirement of HGB measurement. So, this kind of analyzer might still have two channels and/or two reaction cells for two reactions.

The two-channel method might need more blood sample amount and more kinds of regents because of two independent reactions. And this method might have unsatisfied test speed, because two detections might be carried out in sequence. Moreover, a blood analyzer using this method might have more complex structure and larger size because it has two reaction cells, two sets of sample transferring apparatuses.

Therefore, there might be need to continue to develop a low cost and more accurate blood analysis method, control device and blood analyzer.

The scope of the present invention is defined solely by the appended claims, and is not affected to any degree by the statements within this summary.

In one aspect of the present disclosure, there is provided a blood analysis method for a blood cell analyzer, the blood cell analyzer comprising a reaction cell where a testing sample is prepared from a blood sample, and a detection apparatus which detects the testing sample for leukocyte detection, and the method comprising:

injecting a blood sample and a first reagent into the reaction cell, wherein the first reagent lyses erythrocytes in the blood sample and reacts with leukocytes in the blood sample to obtain a first testing sample;

transferring a part of the first testing sample from the reaction cell to the detection apparatus for leukocyte four-group classification detection;

injecting a second reagent into the reaction cell after transferring the part of the first testing sample, wherein the second reagent reacts with leukocytes in a remainder of the first testing sample to obtain a second testing sample; and transferring the second testing sample to the detection apparatus for basophil classification detection.

In another aspect of the present disclosure, there is provided a blood analysis method for a blood cell analyzer, the blood cell analyzer comprising a reaction cell where a testing sample is prepared from a blood sample, and a detection apparatus which detects the testing sample, and the method comprising:

injecting a blood sample and a first reagent in the reaction cell, wherein the first reagent lyses erythrocytes in the blood sample and reacts with leukocytes in the blood sample to obtain a first testing sample;

transferring a part of the first testing sample from the reaction cell to the detection apparatus for leukocyte five-group classification detection;

injecting a second reagent into the reaction cell after transferring the part of the first testing sample, wherein the second reagent reacts with leukocytes in a remainder of the first testing sample to obtain a second testing sample; and measuring the second testing sample for hemoglobin measurement.

In still another aspect of the present disclosure, there is provided a control device for a blood cell analyzer, the blood cell analyzer comprising a reaction cell where a testing sample is prepared from a blood sample, and a detection apparatus which detects the testing sample, and the control device comprising:

a first control unit, which controls a sample injecting apparatus to inject a blood sample into the reaction cell, controls a reagent injecting apparatus to inject a first reagent for leukocyte classification into the reaction cell, wherein the first reagent lyses erythrocytes in the blood sample and reacts with leukocytes in the blood sample to obtain a first testing sample;

a second control unit, which controls a transferring apparatus to transfer a part of the first testing sample from the reaction cell to the detection apparatus for leukocyte four-group classification detection, after the reaction between the blood sample and the first reagent is finished;

a third control unit, which controls the reagent injecting apparatus to inject a second reagent into the reaction cell having a reminder of the first testing sample after the part of the first testing sample is transferred, wherein the reminder of the first testing sample reacts with the second reagent to obtain a second testing sample; and a fourth control unit, which controls the transferring apparatus to transfer the second testing sample to the detection apparatus for basophil classification detection when both leukocyte four-group classification detection and the reaction between the reminder of the first sample and the second reagent are finished.

In still another aspect of the present disclosure, there is provided a control device for a blood cell analyzer, the blood cell analyzer comprising a reaction cell where a testing sample is prepared from a blood sample, and a detection apparatus which detects the testing sample, and said control device comprising:

a first control unit, which controls a sample injecting apparatus to inject a blood sample into the reaction cell, controls a reagent injecting apparatus to inject a first reagent for leukocyte classification into the reaction cell, wherein the first reagent lyses erythrocytes in the blood sample and reacts with leukocytes in the blood sample to obtain a first testing sample;

a second control unit, which controls a transferring apparatus to transfer a part of the first testing sample from the reaction cell to the detection apparatus for leukocyte five-group classification detection, after the reaction between the blood sample and the first reagent is finished;

a third control unit, which controls the reagent injecting apparatus to inject a second reagent into the reaction cell having a reminder of the first testing sample after the part of the first testing sample is transferred, wherein the reminder of the first testing sample reacts with the second reagent to obtain a second testing sample; and a fifth control unit, which controls a hemoglobin measurement apparatus to measure hemoglobin while the reminder of first testing sample reacts with the second reagent.

In still another aspect of the present disclosure, there is provided a blood analyzer which comprising:

a reaction cell, where a testing sample is prepared from a blood sample;

a detection apparatus, which detects the testing sample for leukocyte detection;

a sample injecting apparatus, which injects the blood sample into the reaction cell;

a reagent injecting apparatus, which injects a reagent into the reaction cell;

a transferring apparatus, which transfers the testing sample from the reaction cell to the detection apparatus;

a control device, which couples to the sample injecting apparatus, the reagent injecting apparatus and the transferring apparatus respectively;

wherein the control device controls the sample injecting apparatus to inject a blood sample into the reaction cell, controls the reagent injecting apparatus to inject a first reagent for leukocyte classification into the reaction cell, wherein the first reagent lyses erythrocytes in the blood sample and reacts with leukocytes in the blood sample to obtain a first testing sample;

the control device controls the transferring apparatus to transfer a part of the first testing sample from the reaction cell to the detection apparatus for a leukocyte classification detection after the reaction between the blood sample and the first reagent is finished;

the control device controls the reagent injecting apparatus to inject a second reagent into the reaction cell having a reminder of the first testing sample after the part of the first testing sample is transferred, wherein the reminder of the first testing sample reacts with the second reagent to obtain a second testing sample; and the control device controls the transferring apparatus to transfer the second testing sample to the detection apparatus or a hemoglobin measurement apparatus after the leukocyte classification detection is finished.

In above analyzers, devices and methods, it is disclosed and utilized that a testing sample for leukocyte classification could be further used for basophil classification. After a first reagent reacts with a blood sample to obtain a testing sample for leukocyte detection, a second reagent is added for further reaction to obtain a testing sample for basophil classification or HGB measurement. Therefore, a blood sample may be tested in one reaction cell through time-division multiplexing technology to obtain leukocyte five-group classification result and HGB result by single measurement channel. Thus, the structure of the analyzer may be greatly simplified on the premise of guaranteeing the performance of the analyzer, the volume and cost of the analyzer may reduce and a price-performance ratio of the analyzer may increase.

The following description provides specific details for completely understanding and practicing of embodiments by one skilled in the art. However, those skilled in the art will understand, the embodiment could be practice without some of these details. In order to avoid unnecessarily obscuring descriptions of the embodiments, some of well-known structures and functions are not shown or described in detail in some embodiments. Unless the context clearly requires, otherwise, throughout the specification and claims, the term "comprising", "including" and the like should be inclusive rather than to explain the meaning of an exclusive or exhaustive sense, that is, which means "including, but not limited to". In this detailed description section, a singular or plural terms also include the plural number or singular number.

Figure 1:
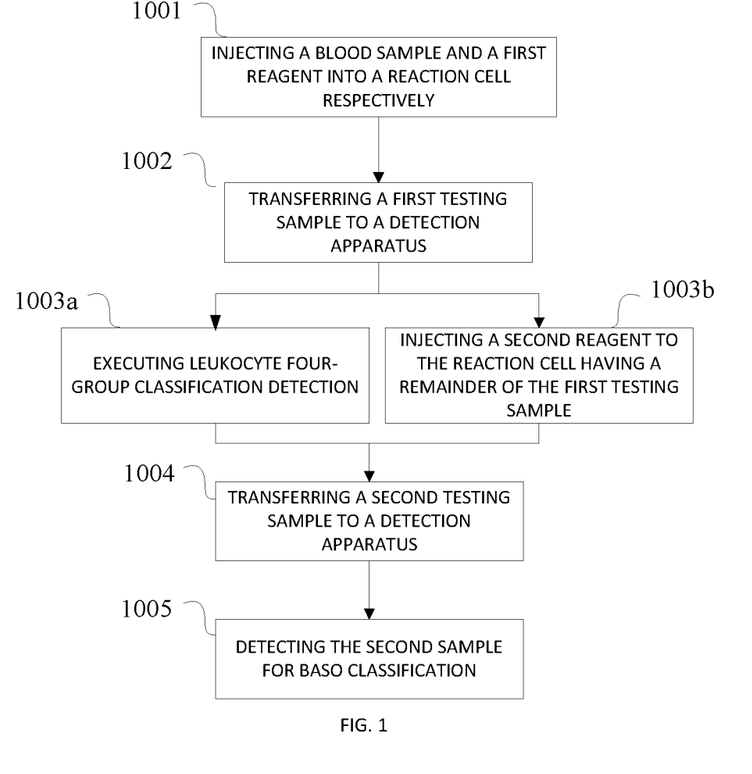
FIG. 1 is a leukocyte detection flowchart in accordance with one embodiment of the present disclosure.

In one embodiment, a blood analyzer includes one set of leukocyte detection channel, which executes two reactions and detections. There is single reaction cell where a testing sample is prepared from a blood sample, single detection apparatus which detects the testing sample for leukocyte detection, a sample injecting apparatus which injects the blood sample into the reaction cell, a reagent injecting apparatus which injects a reagent into the reaction cell, a transferring apparatus and a control device which transfers the testing sample from the reaction cell to the detection apparatus. The control device couples to the sample injecting apparatus, the reagent injecting apparatus and the transferring apparatus respectively. And a leukocyte detection flowchart is shown in FIG. 1, which includes following steps:

step 1001, the control device controls the sample injecting apparatus to inject an amount of the blood sample sufficient for leukocyte detection and basophil detection, and control the reagent injecting apparatus to inject a first reagent for leukocyte classification into the reaction respectively. In the embodiment, the first reagent lyses erythrocytes in the blood sample and reacts with leukocytes so as to make each subclass of leukocytes cluster. The first reagent reacts with the blood sample to obtain a first testing sample.

step 1002, the control device controls the transferring apparatus to transfer a part of the first testing sample from the reaction cell to the detection apparatus after the reaction between the blood sample and the first reagent is finished.

step 1003a, the detection apparatus detects the first testing sample when it passes through the detection apparatus, which is named as a first detection. The first detection is leukocyte four-group classification detection, which means that leukocytes are classified into lymphocyte group, monocyte group, neutrophil & basophil group and eosinophil group and counted respectively based on signals of the detection. After the part of the first testing sample is drawn from the reaction cell, step 1003b is executed. The control device controls the reagent injecting apparatus to inject a second reagent into the reaction cell having a reminder of the first testing sample, and the reminder of the first testing sample reacts with the second reagent to obtain a second testing sample. The second reagent may shrink the other cells except for basophils. The leukocyte classification detection and reaction of the second reagent may begin at the same time; alternatively, one of them may begin firstly, and some of their process may overlap to reduce whole time cost of leukocyte detection.

step 1004, the control device controls the transferring apparatus to transfer a suitable amount of the second testing sample from the reaction cell to the detection apparatus when both leukocyte four-group classification detection and reaction of the second reagent are finished.

step 1005, the detection apparatus detects the first testing sample when it passes through the detection apparatus, which is named as a second detection. The second detection is basophil classification detection, which means that basophils are classified from other cells of leukocytes and counted based on signals of the detection.

Figure 2:
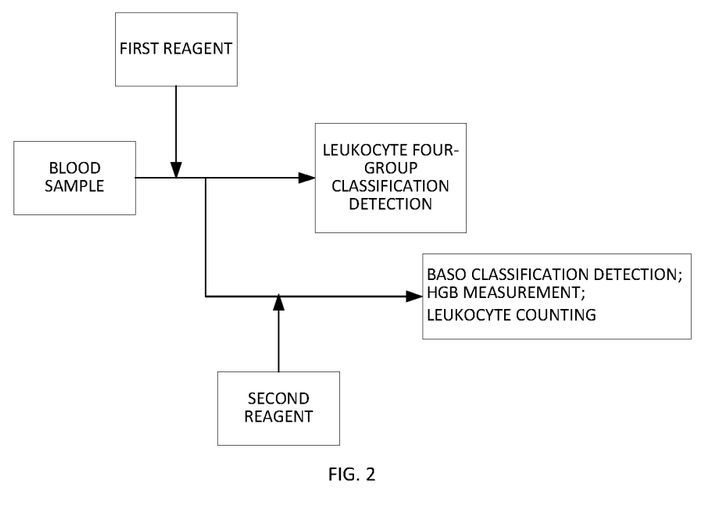
FIG. 2 is a schematic diagram of leukocyte detection in accordance with one embodiment of the present disclosure.
Figure 3:
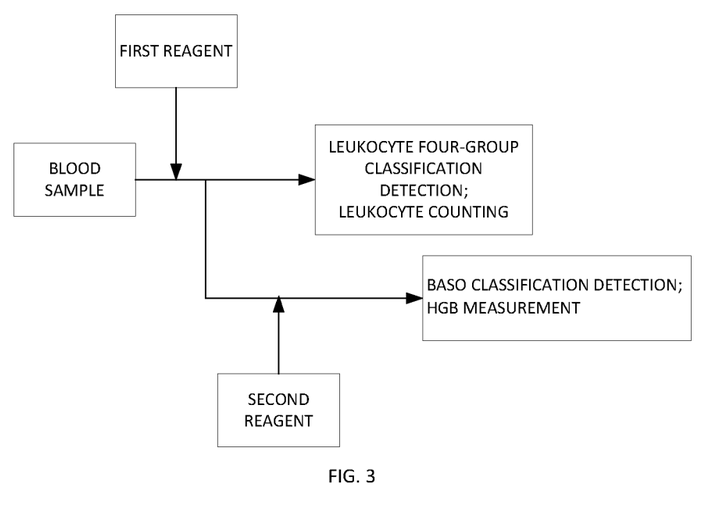
FIG. 3 is schematic diagram of leukocyte detection in accordance with another embodiment of the present disclosure.

When hemoglobin of the blood sample needs to be measured, the second testing sample could be detected for hemoglobin measurement. Moreover, leukocyte counting and classification may be executed simultaneously; in another word, a signal acquired in leukocyte classification detection could be used in leukocyte counting, because difference between subgroups of leukocyte does not influence leukocyte counting. Alternatively, leukocyte counting may be executed based on basophil classification result. Schematic diagrams of leukocyte counting and hemoglobin measurement are shown in FIG. 2 and FIG. 3.

In the embodiment, components or concentrations of the first reagent and second reagent may be irrelative. The first reagent may be single reagent or multi-component reagent whose components are injected into the reaction cell according to a set sequence. The blood sample reacts with the first reagent to obtain the first testing sample. Different first testing sample may be obtained according to different first reagent. In like manner, the second reagent may be single reagent or multi-component reagent. Any reagent which can be used for leukocyte four-group or five-group classification could be named as a first reagent, and any reagent which can be used for basophil classification could be used as a second reagent.

In one embodiment, the transferring apparatus includes a syringe and a transfer pipeline which connects to the syringe, and the syringe, a testing sample outlet of the reaction cell and an inlet of the detection apparatus are connected by the transfer pipeline. There is a cleaning process after the leukocyte classification is finished and before the basophil classification is started, wherein the transfer pipeline and the detection apparatus though which the first testing sample has passed are cleaned to prevent the first testing sample from contaminating the second testing sample.

In the embodiment, leukocytes are classified as follows after the blood sample is tested:

| | |
|---|---|
| Lymphocyte (LYM) | 23.8% |
| Monocyte (MON) | 6.7% |
| Neutrophil (NEU) | 65.4% |
| Eosinophil (ESO) | 3.4% |
| Basophil (BASO) | 0.7% |

Before the sample is tested, the same sample is examined by a conventional microscopy and the result is obtained as follows:

| | |
|---|---|
| Lymphocyte (LYM) | 24% |
| Monocyte (MON) | 7% |
| Neutrophil (NEU) | 65% |
| Eosinophil (ESO) | 3% |
| Basophil (BASO) | 1% |

By comparing these two results, it is shown that the result of the present disclosure corresponds with that of conventional microscopy, and the present disclosure has satisfying accuracy and reliability.

In above method for a blood cell analyzer, two reactions and two detections are executed by single set leukocyte detection channel. The first reaction is executed by mixing the blood sample and a reagent for leukocyte classification, and the second reaction is executed by mixing the first testing sample and a reagent for basophil classification. These two reactions may be executed simultaneously. The first detection is leukocyte four-group classification detection and the second detection is basophil classification detection. After two detections, the results of leukocyte four-group classification and basophil classification are obtained, whose accuracy and reliability could meet requirement. So the method of present disclosure retains advantages of two-channel method. In further, since there is single set leukocyte detection channel in the blood analyzer of the present disclosure, one reaction cell and its correlative injecting, cleaning, discharging, and mixing pipeline may be saved, so that the analyzer may has more simple structure, smaller size and less manufacturing cost in the premise of ensuring analyzer performance. Thus the analyzer has better performance-price ratio. In addition, the blood sample needs to be used in two detection channels in conventional two-channel method. However, the first testing sample is used for further reaction in the method of the present disclosure, so volume of blood sample may decrease and utilization rate of the sample may be improved.

Figure 4:
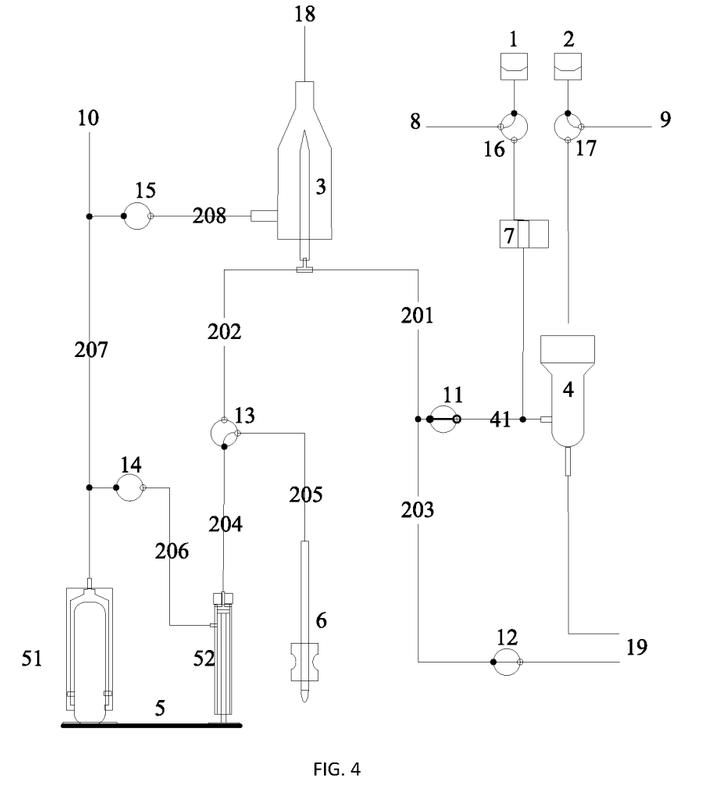
FIG. 4 is structural schematic diagram of a flow cytometer in accordance with one embodiment of the present disclosure.

Light scattering theory is usually used in leukocyte classification. Based on light scattering principle, a blood sample usually undergoes a sampling process, reaction process, sample-preparing process, detection process and cleaning process in a blood analyzer after it is acquired. In one embodiment, a blood analyzer has suitable pipelines and valves, and then two kinds of reagent can be injected into single reaction cell and a testing sample can be transferred successively to a detection apparatus for blood analysis. In another embodiment, as shown in FIG. 4, a blood analyzer includes a reaction cell 4, a detection apparatus 3, a sample injecting apparatus, a reagent injecting apparatus, a transferring apparatus, a cleaning pipeline 203 and a control device (not shown in the drawing).

The sample injecting apparatus injects a blood sample into a reaction cell. In the embodiment, the sample injecting apparatus is sample probe 6. In other embodiments, the sample injecting apparatus may have other structure.

The reagent injecting apparatus injects a reagent into a reaction cell. In the embodiment, the reagent injecting apparatus has two sets of injecting apparatus, such as a first reagent injecting apparatus 1 and a second reagent injecting apparatus 2. The first reagent injecting apparatus 1 and the second reagent injecting apparatus 2 may be a constant flow pump, a pressure source or a syringe. The first reagent injecting apparatus 1 is connected with the reaction cell 4 through a sixth controllable valve 16, and draws a certain amount of reagent from a reagent container 8. In another embodiment, based on user's requirement, the first reagent injecting apparatus 1 may further include a reagent heating apparatus 7 in pipeline between the first reagent injecting apparatus 1 and the reaction cell 4. The second reagent injecting apparatus 2 is connected with the reaction cell 4 by a seventh controllable valve 17, and draws a certain amount of reagent from a reagent container 9. In other embodiments, the reagent injecting apparatus may have single set injecting apparatus.

The transferring apparatus transfers a testing sample from the reaction cell to the detection apparatus. In the embodiment, the transferring apparatus includes a syringe and a transfer pipeline which connects to the syringe. And the syringe, a testing sample outlet of the reaction cell and an inlet of the detection apparatus are connected by the transfer pipeline, and the testing sample outlet has a first controllable valve 11 for controlling "on-off" of the outlet. The syringe may be multiple syringes, which executes drawing and discharging movement based on control of the control device. A first end of the cleaning pipeline 203 connects to the transfer pipeline and the testing sample outlet 41 of the reaction cell, and a second end of the cleaning pipeline 203 connects to a waste collecting apparatus 19, and the cleaning pipeline has a second controllable valve 12 for controlling "on-off" of the cleaning pipeline. The control device couples to the first controllable valve 11 and the second controllable valve 12 respectively for controlling their "on-off". Controlling process of the control device includes steps as follows.

The control device controls the syringe to move after the reaction between the blood sample and the first reagent is finished, to transfer a part of a first testing sample which is prepared by a blood sample and a first reagent from the reaction cell 4 to the detection apparatus 3 by the transfer pipeline. The control device controls the first controllable valve 11 as "on" and the second controllable valve 12 as "off" during the part of the first testing sample is drawn, and controls the first controllable valve 11 as "off" and the second controllable valve 12 keeping "off" after drawing of the part of the first testing sample is finished. The control device controls the first controllable valve 11 keeping "off" and the second controllable valve 12 as "on" after the leukocyte classification detection is finished, and controls the syringe to draw a cleaning solution to clean the transfer pipeline and the detection apparatus 3 and discharge the cleaning solution through the cleaning pipeline. The control device controls the first controllable valve 11 as "on" and the second controllable valve 12 as "off" after both the cleaning and the reaction between the reminder of the first testing sample and the second reagent are finished, and controls the syringe to transfer part of the second testing sample through the transfer pipeline from the reaction cell 4 to the detection apparatus 3. The control device controls the first controllable valve 11 as "off" and the second controllable valve 12 keeping "off" after the drawing of part of the second testing sample is finished.

In the embodiment, the control device includes a first control unit, a second control unit, a third control unit and a fourth control unit. The first control unit controls the sample injecting apparatus to inject an amount of blood sample sufficient for leukocyte detection and basophil detection into the reaction cell, controls the reagent injecting apparatus to inject a first reagent for leukocyte classification into the reaction cell, where the blood sample reacts with the first reagent to obtain a first testing sample. The second control unit controls the transferring apparatus to transfer a part of the first testing sample from the reaction cell to the detection apparatus for leukocyte four-group classification detection, after the reaction between the blood sample and the first reagent is finished. The third control unit controls the reagent injecting apparatus to inject a second reagent into the reaction cell having a reminder of the first testing sample during the leukocyte four-group classification detection, wherein the reminder of the first testing sample reacts with the second reagent to obtain a second testing sample and the second shrinks the other cells except for basophils. The fourth control device controls the transferring apparatus to transfer the second testing sample to the detection apparatus for basophil classification detection when both leukocyte four-group classification detection and reaction of the second reagent are finished.

In the embodiment, a transferring apparatus includes a syringe 5 and a transfer pipeline which connects to the syringe. The syringe 5 includes two syringes; one is a first syringe 51 which is a larger discharge syringe, the other is a second syringe 52 which is a smaller discharge syringe. The transfer pipeline includes sample acquiring pipeline 205, a first sample preparing pipeline 201, a second sample preparing pipeline 202, a second connecting pipeline 204, a first connecting pipeline 207, an auxiliary pushing pipeline 206 and a sheath fluid pipeline 208. The first sample preparing pipeline 201 and the second sample preparing pipeline 202 have a first end and a second end respectively. The first end of the first sample preparing pipeline 201 connects to a testing sample outlet 41 of the reaction cell which has the first controllable valve 11. The second end of the first sample preparing pipeline 201 connects to the first end of the second sample preparing pipeline 202. The first sample preparing pipeline 201 and the second sample preparing pipeline 202 connect to the inlet of the detection apparatus 3 by a three-way valve which is set in a junction of the first sample preparing pipeline 201 and the second sample preparing pipeline 202. The sample acquiring pipeline 205 has a first end a second end, and the first end of the sample acquiring pipeline 205 connects to the sample probe 6. The second connecting pipeline 204 has a first end and a second end, and the first end of the second connecting pipeline 204 connects to the second syringe 52, the second end of the second connecting pipeline 204 connects to the second end of the sample acquiring pipeline 205 and the second end of the second sample preparing pipeline 202 respectively by a third controllable valve 13. The first connecting pipeline 207 has a first end and a second end, and the first end of the first connecting pipeline 207 connects to the first syringe 51, the second end connects to an inlet 10 for a diluent input. The auxiliary pushing pipeline 206 has a first end, a second end and a fourth controllable valve 14, and the first end of the auxiliary pushing pipeline 206 connects to the second connecting pipeline 204, the second end connects to the first connecting pipeline 207. The sheath fluid pipeline 208 has a first end, a second end and a fifth controllable valve 15, and the first end of the sheath fluid pipeline 208 connects to the first connecting pipeline 207, and the second end connects to the detection apparatus 3.

A workflow of a blood cell analyzer according to the embodiment of the present disclosure is as follows.

A blood sample is transferred to the reaction cell 4 by the sample probe 6 under action of the syringe 5, and diluted by a diluent in a certain dilution ratio. The diluent is transferred into the reaction cell 4 through a fourth controllable valve 14, the second sample preparing pipeline 202, the first sample preparing pipeline 201 and the first controllable valve 11. The first reagent is transferred into the reaction cell 4 through a reagent container 8, the sixth controllable valve 16 and the reagent heating apparatus by the first reagent transferring apparatus 1. The first reagent reacts with the solution in the reaction cell 4 for white blood cell (WBC) classification reaction to obtain the first testing sample. After the reaction is finished, the control device controls the third controllable valve 13 to connect the second sample preparing pipeline 202 with the second connecting pipeline 204, and the third controllable valve 13 keeps them connecting after sampling and dividing are finished. A part of the first reaction solution is drawn into the first sample preparing pipeline 201 and the second sample preparing pipeline 202 under drawing action of the syringe 5 for sample preparation. Then, a second reagent is transferred into the reaction cell 4 through reagent container 9 and the seventh controllable valve 17 by the second reagent injecting apparatus 2. The second reagent reacts with a reminder of the first testing sample in the reaction cell for basophil (BASO) reaction to obtain a second testing sample. And during the BASO reaction, hemoglobin (HGB) concentration curve is recorded, and HGB result will be obtained after the reaction becomes stable. At the same time, a diluent is being transferred through a fifth controllable valve 15 under pushing action of the syringe 5, and wraps and carries the first testing sample in the second sample preparing pipeline 202 into the detection apparatus 3 for leukocyte classification detection. The first controllable valve 11 plays a role in blocking so that leukocyte classification detection and BASO reaction can be executed simultaneously. After the leukocyte classification detection and BASO reaction are both finished, the first sample preparing pipeline 201, the second sample preparing pipeline 202 and the detection apparatus 3 are cleaned for subsequent basophil detection. A cleaning pipeline 203 and a second controllable valve 12 are set for cleaning those pipelines through which the sample has passed. A waste sample is discharged into the waste collecting apparatus 19. By this design, the reaction solution for basophil detection in the reaction cell may not affected by the cleaning process. A diluent could be transferred into the detection apparatus 3 for cleaning through the fourth controllable valve 14 and the fifth controllable valve 15. After cleaning process, part of the second testing sample is drawn into the first sample preparing pipeline 201 and the second sample preparing pipeline 202 under drawing action of the syringe 5 for sample preparation. Then the basophil detection is executed in similar manner of the leukocyte classification detection. The diluent is wrapping and carrying the second testing sample in the second sample preparing pipeline 202 into the detection apparatus 3 for basophil detection, when the diluent is being transferred under pushing action of the syringe 5. Leukocyte counting result may be obtained by leukocyte classification detection or basophil detection.

In the embodiment, the transferring apparatus only has one first syringe and one second syringe. The first syringe could be used in providing sheath fluid, drawing testing sample from the reaction cell or providing cleaning solution. The second syringe could be used in acquiring sample or providing sample fluid in detection. So the syringes are repetitive-used. And with help of suitable pipeline design, number of controllable valve may be reduced and structure of fluid road may be simplified under the premise of ensuring performances of sample acquiring, sample preparing, cell detection in flow cytometry, cleaning and etc.

In another embodiment, the first syringe and the second syringe may be joined syringe having a common drive. The common drive makes the first and second syringes drawing and discharging simultaneously, so one set of electric motor and drive mechanism may be saved. Before sample acquiring, the fourth controllable valve 14 should be off status so that the sample probe would not be affected by the first syringe 51 when they draw liquid. In other embodiments, the first syringe and second syringe may be driven by two independent drives.

In other embodiments, the transferring apparatus may have other fluid road structure. The first syringe and second syringe may have single use. For example, the first syringe for providing sheath fluid may be independent of that for drawing testing sample, or that of providing cleaning solution. Likewise, the second syringe for acquiring sample may be independent of that of providing sample fluid in detection. So in these kinds of embodiments, the transferring apparatus may have a plurality of first syringe and second syringe, and fluid road structure may be different according to different usage of these syringes.

Figure 5:
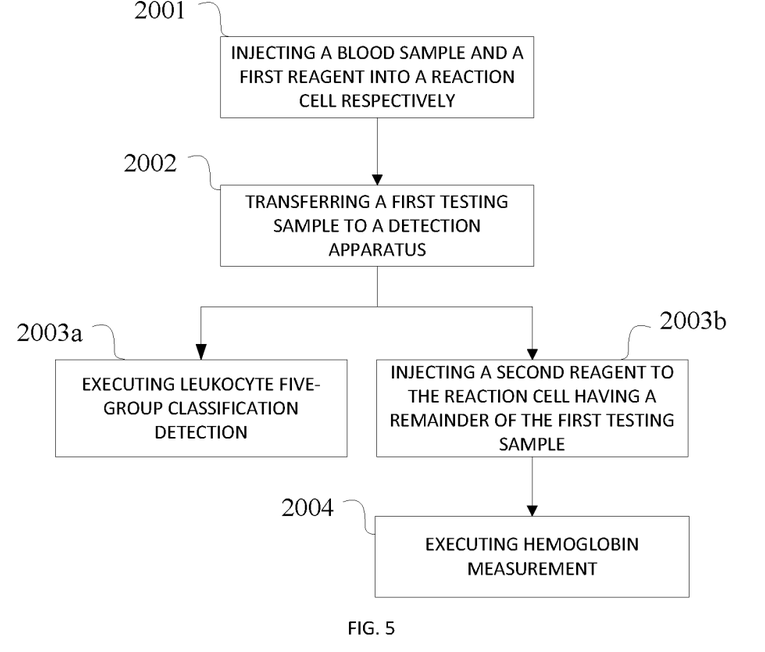
FIG. 5 is a leukocyte detection flowchart in accordance with another embodiment of the present disclosure in accordance with another embodiment of the present disclosure.

In still another embodiment, a first testing sample may be detected for leukocyte five-group classification and may be mixed with a second reagent for further reaction for HGB measurement. So leukocyte five-group classification and HGB measurement may be also achieved by one channel through time-division multiplexing technology. So structure of the blood analyzer may be simplified and size may be smaller. In one embodiment, a detection flowchart is shown in FIG. 5, which includes following steps:

step 2001, the control device controls the sample injecting apparatus to inject an amount of the blood sample sufficient for leukocyte detection and basophil detection, and control the reagent injecting apparatus to inject a first reagent for leukocyte five-group classification into the reaction respectively. The first reagent reacts with the blood sample to obtain a first testing sample.

step 2002, the control device controls a transferring apparatus to transfer a part of the first testing sample from the reaction cell to the detection apparatus after the reaction between the blood sample and the first reagent is finished.

step 2003*a*, the detection apparatus detects the first testing sample when it passes through the detection apparatus, which is name as a first detection. The first detection is leukocyte five-group classification detection, which means that leukocytes are classified into lymphocyte group, monocyte group, neutrophil group, basophil group and eosinophil group and respectively counted based on signals of the detection. After the part of the first testing sample is transferred from the reaction cell, step 2003*b* is executed. The control device controls the reagent injecting apparatus to inject a second reagent into the reaction cell having a reminder of the first testing sample, and the reminder of the first testing sample reacts with the second reagent to obtain a second testing sample. The leukocyte classification detection and reaction of the second reagent may be started at the same time; alternatively, one of them may begin firstly, and some of their process may overlap to reduce whole time cost of leukocyte detection.

step 2004, the control device controls a hemoglobin measurement apparatus to execute hemoglobin measurement when the first testing sample reacts with the second reagent.

Figure 6:
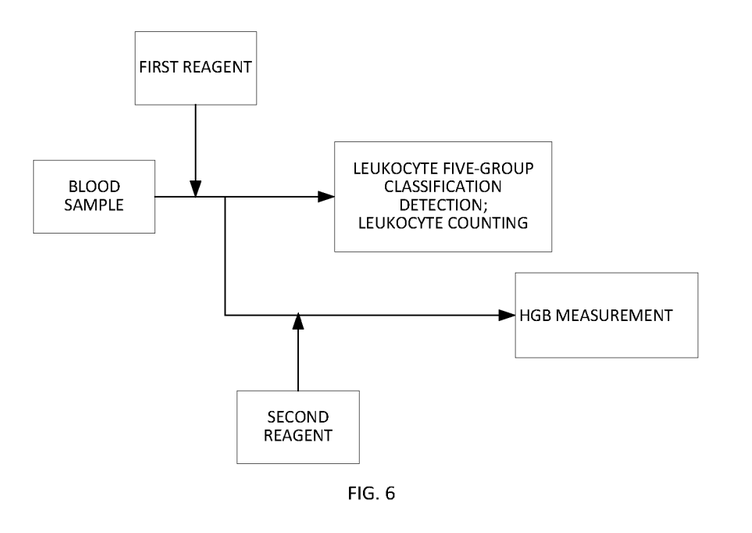
FIG. 6 is a schematic diagram of leukocyte detection in accordance with one embodiment of the present disclosure.
Figure 7:
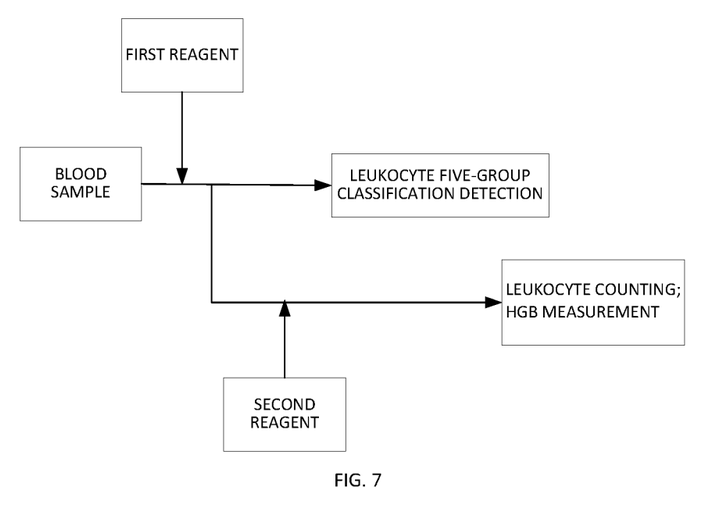
FIG. 7 is schematic diagram of leukocyte detection in accordance with another embodiment of the present disclosure.

In the embodiment, leukocyte counting may be executed beside hemoglobin measurement. The leukocyte counting may be executed based on signs acquired during leukocyte five-group classification detection, as shown in FIG. 6. Alternatively, the testing sample mixed with a second reagent may be detected for leukocyte counting, as shown in FIG. 7.

In the embodiment, the control device includes a first control unit, a second control unit, a third control unit and a fifth control unit. The first control unit controls the sample injecting apparatus to inject an amount of blood sample sufficient for leukocyte detection and basophil detection into the reaction cell, controls the reagent injecting apparatus to inject a first reagent for leukocyte classification into the reaction cell, wherein the first reagent reacts with leukocytes in the blood sample to obtain a first testing sample. The second control unit controls the transferring apparatus to transfer a part of the first testing sample from the reaction cell to the detection apparatus for leukocyte five-group classification detection, after the reaction between the blood sample and the first reagent is finished. The third control unit controls the reagent injecting apparatus to inject a second reagent into the reaction cell having a reminder of the first testing sample during the leukocyte classification detection, wherein the reminder of the first testing sample reacts with the second reagent to obtain a second testing sample. The fifth control unit controls the hemoglobin measurement apparatus to measure hemoglobin while the reminder of first testing sample reacts with the second reagent.

In the embodiment, the second reagent is a reagent that could react with the first testing sample to obtain the second testing sample for hemoglobin measurement. The second reagent may be single reagent or multi-component reagent whose components are injected into the reaction cell according to a set sequence. A reagent for hemoglobin measurement may be the same as or different from that for basophil classification.

The blood analyzer of the present disclosure may save a set of reaction cell and pipelines thereof. Moreover, the blood analyzer may maintain the same or similar performance of a blood analyzer using the two-channel method. So the blood analyzer may have better performance-price ratio than conventional analyzer.

The above embodiments illustrates various features of the present disclosure, which are described in detail, but is not intended to in any way limit the scope of the invention as set forth in the claims. It will be appreciated by those skilled in the art that various changes, alterations and modifications may be made to the present disclosure without departing from the spirit and scope of the present disclosure as claimed. Accordingly, the scope of the present invention patent protection should defined solely by the appended claims.

The invention claimed is:

1. A blood analyzer comprising:
a single reaction cell for leukocyte classification, where a first testing sample and a second testing sample are successively prepared in the single reaction cell from a blood sample for leukocyte four-group classification detection and for basophil classification detection, respectively;
a detection apparatus connecting with the single reaction cell;
a sample injecting apparatus;
at least one reagent injecting apparatus connecting with the single reaction cell;
a transferring apparatus; and
a control device coupled with the detection apparatus, the sample injecting apparatus, the at least one reagent injecting apparatus and the transferring apparatus, respectively;
wherein the control device is programmed to:
control the sample injecting apparatus to deliver the blood sample into the single reaction cell;
control the at least one reagent injecting apparatus to deliver a first reagent into the single reaction cell to prepare the first testing sample for a first detection;
after preparation of the first testing sample, control the transferring apparatus to transfer at least a portion of the first testing sample from the single reaction cell to the detection apparatus for the first detection;
control the detection apparatus to perform the first detection of the at least a portion of the first testing sample;
control the at least one reagent injecting apparatus to deliver a second reagent into the single reaction cell to prepare the second testing sample for a second detection;
after preparation of the second testing sample, control the transferring apparatus to transfer at least a portion of the second testing sample from the single reaction cell to the detection apparatus for the second detection; and
control the detection apparatus to perform the second detection of the at least a portion of the second testing sample;
wherein the transferring apparatus comprises a syringe coupled with the control device and a transfer pipeline connected with the syringe; a testing sample outlet of the single reaction cell and an inlet of the detection apparatus are connected by the transfer pipeline, and the testing sample outlet has a first controllable valve for controlling "on-off" of the outlet.

2. The blood analyzer according to claim 1, wherein the at least one reagent injecting apparatus includes a first and a second reagent injecting apparatus, each connecting with the single reaction cell respectively, the control device is programmed to control the first reagent injecting apparatus to deliver the first reagent into the single reaction cell to prepare the first testing sample, and control the second reagent injecting apparatus to subsequently deliver the second reagent into the single reaction cell to prepare the second testing sample after the first testing sample is transferred for detection.

3. The blood analyzer according to claim 1, said blood analyzer further comprising a hemoglobin measurement apparatus connecting with the single reaction cell, wherein the control device is programmed to control the hemoglobin measurement apparatus to perform hemoglobin measurement of the second testing sample.

4. The blood analyzer according to claim 1, wherein said detection apparatus is an optical detection apparatus.

5. The blood analyzer according to claim 1, wherein said detection apparatus comprises an optical detection apparatus for performing the first detection and an impedance detection apparatus for performing the second detection.

6. The blood analyzer according to claim 1, wherein said blood analyzer further comprising a cleaning pipeline, the control device is programmed to control the cleaning pipeline to clean the transfer pipeline and the detection apparatus, wherein:
    a first end of the cleaning pipeline is connected with the transfer pipeline and the testing sample outlet of the single reaction cell, and a second end of the cleaning pipeline is connected with a waste collecting apparatus, and the cleaning pipeline has a second controllable valve for controlling "on-off" of the cleaning pipeline; and
    the control device is coupled with the first controllable valve for controlling "on-off" of the testing sample outlet and the second controllable valve for controlling "on-off" of the cleaning pipeline.

7. The blood analyzer according to claim 1, wherein said syringe comprising:
    at least one first syringe and at least one second syringe;
    the control device is programmed to control the at least one first syringe to provide sheath fluid, draw the testing sample from the single reaction cell and/or provide cleaning solution, and
    the control device is programmed to control the at least one second syringe to draw the blood sample from the sample injecting apparatus and/or provide sample fluid in detection.

8. The blood analyzer according to claim 7, wherein the at least one first syringe and the at least one second syringe are capable of being driven by a common drive.

9. The blood analyzer according to claim 7, wherein the at least one first syringe and the at least one second syringe are capable of being driven by different drives.

10. The blood analyzer according to claim 1, wherein said syringe comprising at least one first syringe and at least one second syringe, the sample injecting apparatus comprises a sample probe and the transfer pipeline comprises:
    a sample acquiring pipeline having a first end connected with the sample probe and a second end connected with the at least one second syringe;
    a first sample preparing pipeline having a first end connected with the testing sample outlet of the single reaction cell and a second end connected with the inlet of the detection apparatus;
    a second sample preparing pipeline having a first end connected with the inlet of the detection apparatus and a second end connected with the at least one second syringe;
    a first connecting pipeline having a first end connected with the at least one first syringe and a second end connected with an inlet for a diluent input;
    a second connecting pipeline having a first end connected with the at least one second syringe and a second end connected with the second end of the sample acquiring pipeline and the second end of the second sample preparing pipeline respectively by a third controllable valve;
    an auxiliary pushing pipeline having a first end connected with the second connecting pipeline, a second end connected with the first connecting pipeline and a fourth controllable valve for controlling "on-off" of the auxiliary pushing pipeline; and
    a sheath fluid pipeline having a first end connected with the first connecting pipeline, a second end connected with the detection apparatus and a fifth controllable valve for controlling "on-off" of the sheath fluid pipeline.

* * * * *